United States Patent
Angel

(10) Patent No.: US 9,937,102 B2
(45) Date of Patent: Apr. 10, 2018

(54) SELF-EXPANDABLE TUBE AND METHOD OF USE

(71) Applicant: BIO2 MEDICAL, INC., San Antonio, TX (US)

(72) Inventor: Luis F. Angel, San Antonio, TX (US)

(73) Assignee: BIO2 MEDICAL, INC., Golden, CO (US)

( * ) Notice: Subject to any disclaimer, the term of this patent is extended or adjusted under 35 U.S.C. 154(b) by 949 days.

(21) Appl. No.: 14/307,431

(22) Filed: Jun. 17, 2014

(65) Prior Publication Data
US 2014/0371678 A1 Dec. 18, 2014

Related U.S. Application Data

(60) Provisional application No. 61/835,993, filed on Jun. 17, 2013.

(51) Int. Cl.
| | | |
|---|---|---|
| *A61M 5/00* | (2006.01) | |
| *A61J 15/00* | (2006.01) | |
| *A61M 1/00* | (2006.01) | |
| *A61M 25/00* | (2006.01) | |

(52) U.S. Cl.
CPC ....... *A61J 15/0003* (2013.01); *A61J 15/0046* (2013.01); *A61J 15/0069* (2013.01); *A61J 15/0073* (2013.01); *A61M 1/008* (2013.01); *A61M 2025/0024* (2013.01); *A61M 2025/0037* (2013.01)

(58) Field of Classification Search
CPC ........... A61J 15/0003; A61J 15/0046; A61J 15/0069; A61J 15/0073; A61M 1/008; A61M 2025/0024; A61M 2025/0037
USPC ............................................ 604/171
See application file for complete search history.

(56) References Cited

U.S. PATENT DOCUMENTS

| | | | | |
|---|---|---|---|---|
| 5,791,341 | A | 8/1998 | Bullard | 128/207 |
| 5,803,080 | A | 9/1998 | Freitag | 128/207.14 |
| 5,893,868 | A | 4/1999 | Hanson et al. | 606/198 |
| 6,506,179 | B1 * | 1/2003 | Tiefenthal | A61M 25/04 |
| | | | | 604/103.06 |
| 2003/0149444 | A1 * | 8/2003 | Khaw | A61F 2/954 |
| | | | | 606/194 |
| 2008/0156323 | A1 * | 7/2008 | Angel | A61M 16/04 |
| | | | | 128/200.26 |
| 2009/0216186 | A1 * | 8/2009 | Nath | A61J 15/0015 |
| | | | | 604/97.02 |

* cited by examiner

*Primary Examiner* — Jason Flick
(74) *Attorney, Agent, or Firm* — David G. Rosenbaum; J. Peter Paredes; Rosenbaum IP, P.C.

(57) ABSTRACT

The invention relates to a self-expandable tube having a catheter body with a double lumen in which one lumen allows for suctioning or decompression and another lumen for a feeding tube. A self-expandable portion collects secretions above the expandable portion or in the anatomical lumen and a suction source coupled to the self-expandable tube removes the secretions as is disclosed herein.

15 Claims, 3 Drawing Sheets

SELF-EXPANDABLE TUBE AND METHOD OF USE

CROSS-REFERENCE TO RELATED APPLICATIONS

The present application claims priority to U.S. Provisional Application Ser. No. 61/835,993, filed Jun. 17, 2013, which is hereby incorporated by reference in its entirety.

BACKGROUND

The embodiments described herein generally relate to a self-expandable tube that may be used within the anatomical lumen of the body. A self-expandable tube may be used for multiple purposes. For example, the self-expandable tube may be used in an angioplasty procedure to capture and remove arterial plaque in a patient's vasculature. A self-expandable tube can also be used as a feeding tube, which inhibits the reflux of gastric material into the lungs for example.

Feeding tubes are traditionally placed in the stomach or the post-pyloric area and one of the main concerns is the aspiration of gastric material into the upper airways and into the lungs. These tubes are used in almost all the patients requiring mechanical ventilation and critical care support. The present invention solves these problems as well as others.

SUMMARY OF THE INVENTION

Provided herein are systems, methods, and apparatuses for a Self-Expandable Tube.

The self-expandable tube has a proximal end and a distal end. At the distal end of the self-expandable tube is a self-expandable portion which can contract during insertion and expand to the size of the anatomical lumen to form a sealing membrane. The self-expandable portion is made of biocompatible material which facilitates the contraction and expansion. The self-expandable portion may be coupled onto the catheter body by a reinforcing member. The catheter body includes a first lumen and a second lumen that span the longitudinal length of the catheter body. The first lumen may be coupled with a feeding tube that traverses the length of the first lumen through the self-expandable portion. The second lumen may be coupled with a suctioning or decompression tube that traverses the length of the second lumen through the self-expandable portion. An outer sheath surrounds the catheter body and includes a plurality of openings, which are substantially located on the distal end. There is space between the catheter body and the outer sheath, which allows fluid to flow therebetween. A vacuum or suction source is coupled at the proximal end of the outer sheath.

The self-expandable tube according to the present invention can be placed within any anatomical lumen. The self-expandable portion of the self-expandable tube is in a collapsed state when it is being positioned within the patient. Once the self-expandable tube is fully inserted and properly positioned, the self-expandable portion may be expanded to the size of the anatomical lumen in order to create a sealing membrane. One embodiment of the present invention is a self-expandable tube in which the first lumen may be coupled with a feeding tube and the second lumen with a suction source. The self-expandable tube is inserted through the esophagus, in which the self-expandable portion expands to the size of the esophagus, which inhibits the reflux of gastric materials. Gastric materials that are in the esophagus or accumulate above the self-expandable portion are suctioned through the perforated sheath by a suction source or vacuum. The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

DETAILED DESCRIPTION OF THE INVENTION

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Generally speaking, the Self-Expandable Tube 100 will be placed in the distal third of the esophagus and will expand to the vessel size of the esophagus preventing secretions from the stomach to reflux into the oropharynx and/or lungs. Alternatively, the Self-Expandable Tube 100 may be placed in other locations within the esophagus or other locations within any anatomical lumen. For example, the Self-Expandable Tube 100 may be used within the digestive system, circulatory system, etc. The Self-Expandable Tube 100 creates a seal around the esophagus that will significantly decrease aspiration and potential pneumonias. In one embodiment, the Self-Expandable Tube 100 has a first lumen 120 that allows the placement of a smaller feeding tube 122 in the distal stomach and/or post pyloric area. These feeding tubes are used in almost all the patients requiring mechanical ventilation and critical care support. The anatomical lumen may be an interior of a vessel, such as the central space in an artery or vein through which blood flows. the interior of the gastrointestinal tract, the pathways of the bronchi in the lungs, the interior of renal tubules and urinary collecting ducts, the pathways of the female genital tract, starting with a single pathway of the vagina, splitting up in two lumens in the uterus, both of which continue through the fallopian tubes. The self-expandable tube 100 may be used in connection with a filter system, such as the one described in U.S. Pat. Nos. 8,668,712, 8,613,753, and 8,777,977.

Figure 1:
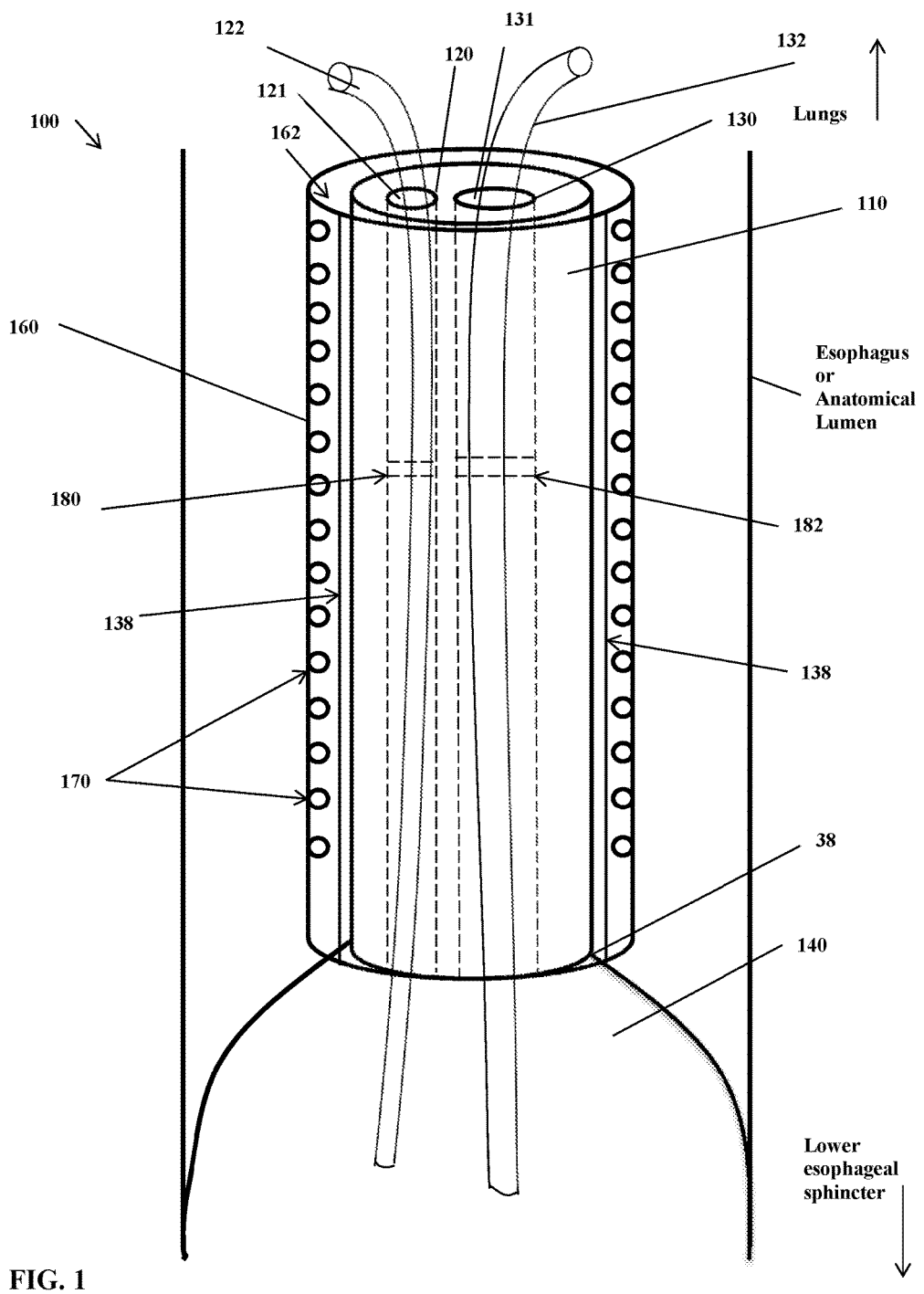
FIG. 1 is an enlarged cross-sectional view of one embodiment of the Self-Expandable, Tube.
Figure 2:
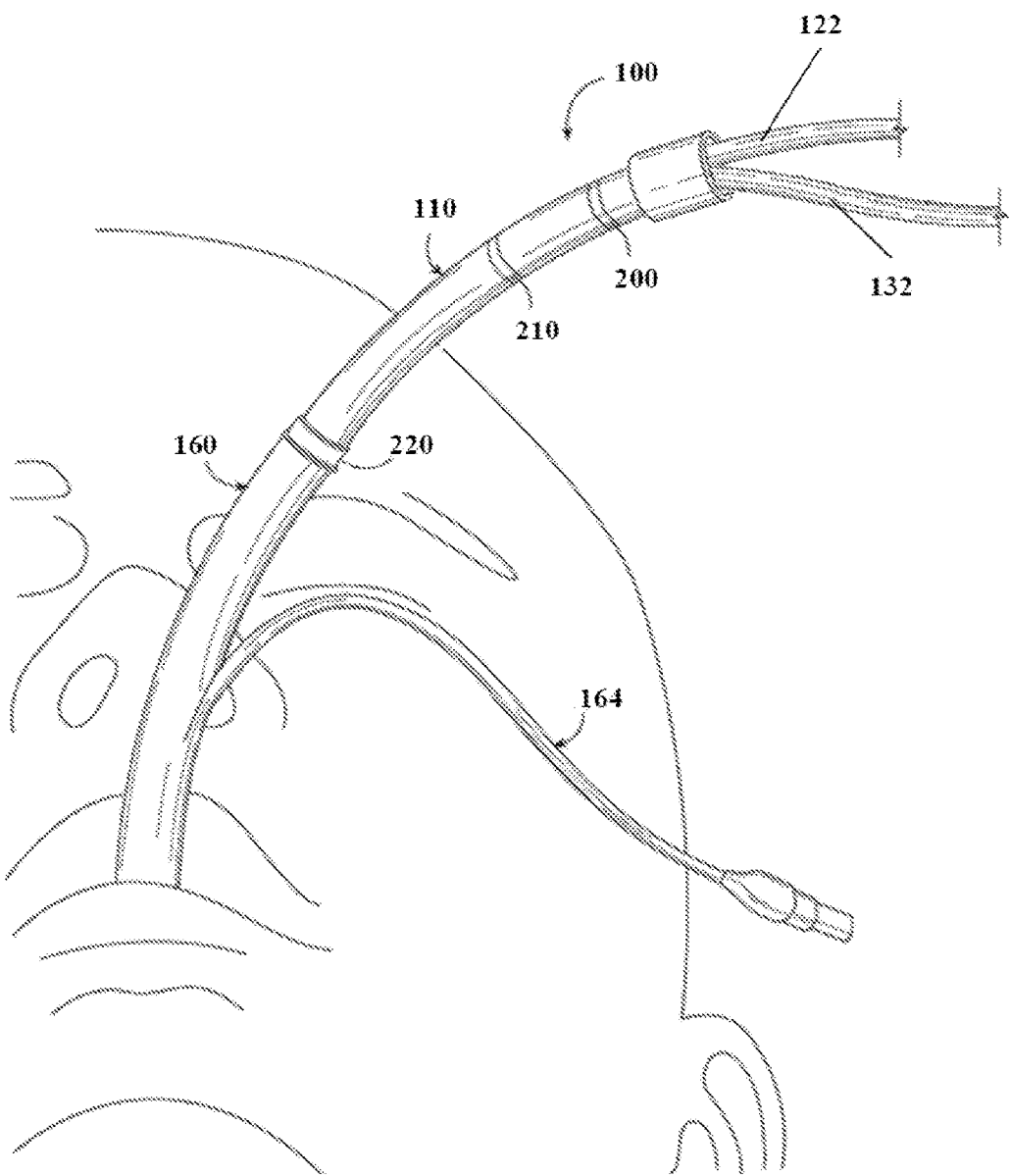
FIG. 2 is a diagrammatic view of a proximal portion of the Self-Expandable Tube as used with a patient.
Figure 3:
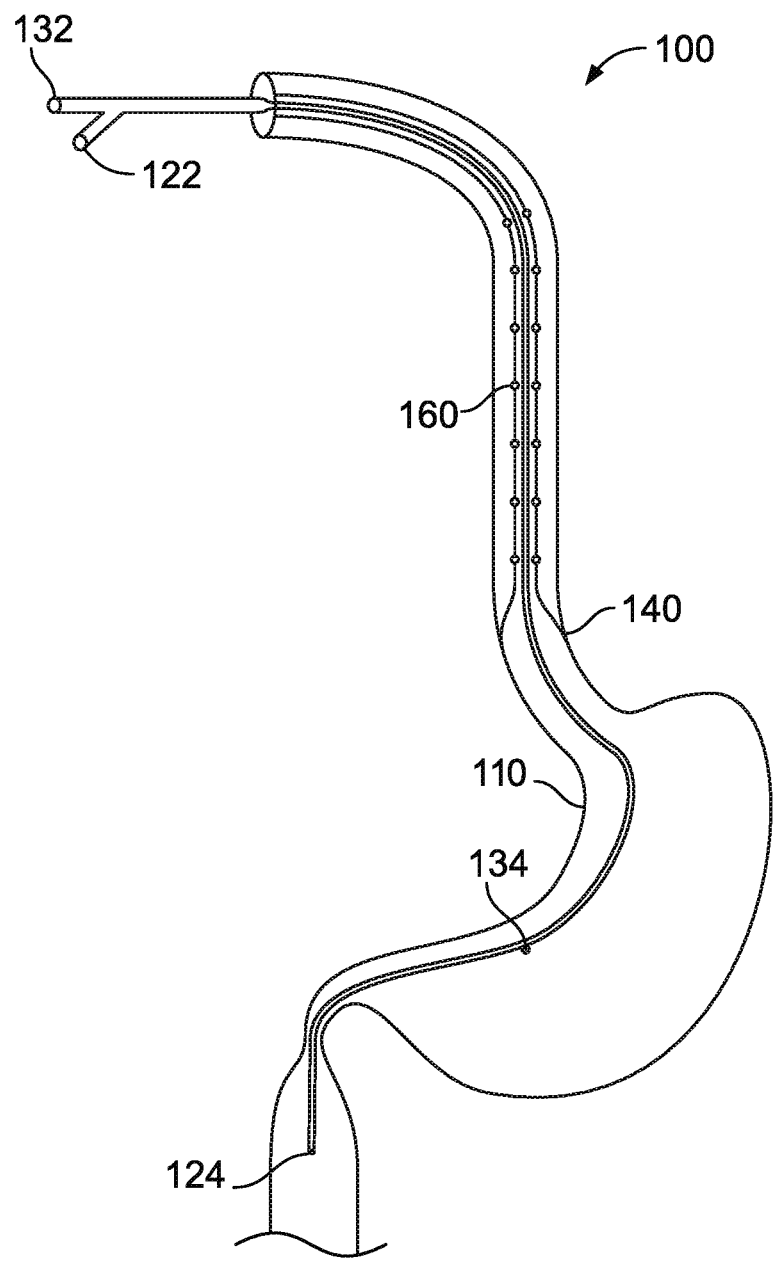
FIG. 3 is a schematic view of one embodiment of the Self-Expandable Tube disposed within a patient.

As shown in FIG. 1, the Self-Expandable Tube 100 includes a catheter body 110 including a self-expandable portion 140 located on the distal end of the catheter body 110. The catheter body 110 includes a first lumen 120 and a second lumen 130 that span the longitudinal length of the catheter body 110. An outer sheath 160 surrounds at least a portion of the longitudinal length of the catheter body 110, and the outer sheath 160 includes a plurality of openings 170 traversing the thickness of the outer sheath 160. Preferably, the plurality of openings 170 are substantially positioned on the distal end of the outer sheath 160 and communicate with a space 162 between the catheter body 110 and the outer sheath 160 to allow fluid to flow therebetween and suctioned to the proximal portion of the Self-Expandable Tube 100. The catheter body 110 and the outer sheath 160 may include a generally tubular configuration, although other polygonal or elliptical configurations are envisioned as well. The proximal portion of the outer sheath 160 is operably coupled to a vacuum or suction source, as shown in FIG. 2, to remove secretions accumulated above the self-expandable portion 140 by suctioning the secretions into the space 162. The first lumen 120 may be operably coupled with a feeding tube 122 that traverses the length of the first lumen 120 through the self-expandable portion 140 and into the distal stomach or post-pyloric area, as shown in FIG. 3. The second lumen 130 may be operably coupled with a suctioning or decompression tube 132 that allows for the suctioning or decompression through the self-expandable portion 140 and into the stomach, as shown in FIG. 3. In one embodiment, the lumens 120, 130 may be bendable along their longitudinal axis to allow for the curvature or bending of the esophagus or other lumen. In one embodiment, the lumens 120, 130 may bend at an angle of between about 0-45 degrees from the longitudinal axis, alternatively, between about 5-35 degrees from the longitudinal axis, alternatively, between about 10-25 degrees from the longitudinal axis. In one embodiment, the feeding tube 122 and the suctioning tube 132 are operably coupled within the same catheter body 110 and operate by way of the first lumen 120 operably coupled to a first distal port 124 and the second lumen 130 operably coupled to a second distal port 134, as shown in FIG. 3. The proximal ports 121 and 131 of the first and second lumens 120, 130 may be sized as to receive the feeding tube 122 and the suction tube 132 and allow longitudinal movement therebetween. Optionally, there may be a seal on the proximal ports 121, 131 to prevent back flow of gastric contents, air, or gas. The second lumen 130 may be larger than the first lumen 120, as to provide the suctioning and clearing of any aspirated materials in the anatomical lumen, such as the gastric contents of the stomach for example. The first lumen 120 may include a first one way valve 180 that allows air to flow distally but prevents fluids from flowing proximally. The second lumen 130 may include a second one way valve 182 that allows air to flow distally but prevents fluids from flowing proximally. The first and second one way valves 180, 182 may be positioned along the length of the first and second lumens 120, 130. Additional valves may be placed along the longitudinal length of the inner lumens 120, 130. Alternatively, the valves may be placed along the distal end of the inner lumens 120, 130 as to be in proximity to the lower esophageal sphincter if acid reflux should be an issue and to prevent vomiting. The expandable portion 140 expands to the size of the anatomical lumen and can be compressed or expanded following contractions and relaxations of the anatomical lumen. The self-expandable portion 140 may have appropriate dimensions in length, diameter, or in its cross-sectional expansive shape, all of which depend on the patient criteria or the anatomy of the anatomical lumen. In one embodiment, the Self-Expandable Tube 100 is inserted into the esophagus and the self-expandable portion 140 is positioned above the lower esophageal sphincter. For purposes of example only, one set of dimensions for the self-expandable portion 140 includes a contracted state that may be between 2-3 mm in diameter, and can expand to the size of the esophagus, which may between 12-14 mm in diameter. In alternative embodiments, the self-expandable portion 140 may expand in order to accommodate a wide variety of variances in anatomical structures.

In one embodiment, the distal end of the outer sheath 160 may abut with the self-expandable portion 140 in the expanded state, as shown in FIG. 1. In another embodiment, the distal end of the outer sheath 160 may be sealed against the catheter body proximal to the self-expandable portion 140. In one embodiment, the outer sheath 160 may conceal the self-expandable portion 140 in the contracted state and the outer sheath 160 may be moved proximally as to expose the contracted self-expandable portion 140 to allow for self-expansion to the expanded state.

The self-expandable portion 140 is preferably fabricated of a biocompatible material, such as silicone or biocompatible metal, which is suitable for use in an anatomical lumen. The self-expandable portion 140 may be fabricated using a single material, wherein the seal is formed as a single monolithic or unitary element, or of plural joined elements formed of the same biocompatible material, such a stent or mesh structure. Alternatively, the self-expandable portion 140 may be fabricated of plural biocompatible materials and may be joined as a composite. In either construct of the self-expandable portion 140, but more preferably, in the case of a composite construction of the self-expandable portion 140, at least one reinforcing member 138 is operably associated with the self-expandable portion 140 to facilitate movement of the self-expandable portion 140 between its diametrically collapsed and diametrically expanded positions. In accordance with the illustrated embodiments, plural reinforcing members 138 are associated with the self-expandable portion 140 and extend longitudinally along the self-expandable portion 140 in a radially spaced apart relationship relative to each other. The at least one reinforcing member 138 may be coupled to the self-expandable portion 140 on either its luminal or abluminal surfaces, or may be embedded within self-expandable portion 140 such that it resides at least partially within a wall thickness of the self-expandable portion 140. Alternatively, the at least one reinforcing member 138 may comprise a relatively thickened region, such as a rib or a pattern or ribs, of the same material employed in fabricating the self-expandable portion 140. The at least one self-expandable portion 140 is preferably an elastic, shape memory or super-elastic material, such as stainless steel, silicone, nitinol, chromium-molybdenum alloys, or similar materials. In this manner the self-expandable portion 140 is self-expanding upon being released from a constraining sheath or covering, such as the self-expandable tube 100. For purposes of this application, when reference is made to self-expandable portion 140, such reference is intended to be inclusive of the at least one reinforcing member 138, where appropriate. Those of ordinary skill in the art will understand that the at least one reinforcing member 138 may or may not be necessary, depending upon the construction and materials employed in fabricating the self-expandable portion 140, in order to provide for either expansion or collapse, or to facilitate or aid in apposition or sealing of the self-expandable portion 140 against the anatomical lumen. The self-expansion may be achieved by a shape memory metal or polymer, which transitions to the larger expanded state upon a present condition, such as temperature, pressure, and the like.

When in its diametrically expanded position, the self-expandable portion 140 is intended to achieve the size of the anatomical lumen while exerting low pressure against the anatomical lumen wall, thereby inhibiting passage of secretions beyond the self-expandable portion 140 to areas of the esophagus proximal the self-expandable portion 140 and improving clearance from secretions deposited proximal of the self-expandable portion 140. The self-expandable portion 140 also reduces the likelihood of unintended fluid passage through the esophagus. In some embodiments, the self-expandable portion 140 may include at least one radiopaque or fluoroscopic marker to facilitate imaging the position of the self-expandable portion 140 after placement. The self-expandable portion 140 may take on any appropriate shape, for instance, the self-expandable portion 140 can be substantially elongated, substantially rounded or substantially horseshoe shape in transverse cross section. In longitudinal aspect, self-expandable portion 140 preferably has an elongate generally tubular shape with a rounded taper at a proximal end thereof that connects with the distal end of the catheter body 110. In one embodiment, the shape of the self-expandable portion 140 may be dictated by airway anatomy, by compatibility with the cough mechanism and by a need to reduce the likelihood of aspiration of secretions. In some embodiments, a distal portion of the self-expandable portion 140, sometimes measuring about 2 to about 3 mm in axial length, may be everted to afford a smoother circumferential surface area for tissue engagement. Everting a distal portion of the self-expandable portion 140 may reduce potential tissue growth around the self-expandable portion 140, and possibly facilitate advancement of the inner lumens 120, 130 with reduced risk of trauma to the patient.

To further facilitate introduction and maneuvering of the Self-Expandable Tube 100, portions of the catheter body 110 and the outer sheath 160 may be comprised of different materials having different physical and/or material properties. For example, proximal portions of the catheter body 110 and outer sheath 160 may be stiffer and more rigid than distal portions of the catheter body 110 and outer sheath 160. This construction may ease the advancement of the Self-Expandable Tube 100 in the patient with reduced deformation or curving of the catheter body 110 and outer sheath 160. Further, the relatively softer and more malleable material comprising the distal portions of the catheter body 110 and outer sheath 160 may allow for deformation or compression of distal ends of the catheter body 110 and outer sheath 160, and also may be more accommodating to the operator.

As shown in FIG. 2, the Self-Expandable Tube 100, including catheter body 110 and outer sheath 160, is prepared for insertion into a patient to prevent secretions from the lower GI into the patient's oropharynx and/or lungs. Positioning marks may be placed on the catheter body 110 to indicate the relative positions of the catheter body 110 and the outer sheath 160 and whether the Self-Expandable Tube 100 is above the lower esophageal sphincter but below the lungs. A first positioning mark 200 and a second positioning mark 210 indicate the status of the self-expandable portion 140. Specifically, the first positioning mark 200 is provided distally to indicate that the self-expandable portion 140 is in the contracted state, and the second positioning mark 210 is provided proximally to indicate that the self-expandable portion 140 is expanded. The outer sheath 160 may include a coupling for a vacuum source 164 that suctions the secretions accumulated above the self-expandable portion 140. The proximal portion of the catheter body 110 may include a hub portion 220 for stopping the distal movement of the catheter body 110. The proximal portions of the feeding tube 122 and the suction tube 132 are operably coupled with the proximal portion of the catheter body 110.

As shown in FIG. 3, the Self-Expandable Tube 100, including catheter body 110 and outer sheath 160 in an alternative embodiment whereby the catheter body 110 extends through the expandable portion 140, the stomach portion, and past the post-pyloric area. The catheter body 110 includes the first lumen 120 and the second lumen 130; however, the first lumen 120 includes a first distal port 124 that is located in the post-pyloric stomach area, and the second lumen 130 includes a second distal port 134 that is located in the stomach area. The expandable portion 140 expands in the distal third of the esophagus to the vessel size of the esophagus preventing secretions from the stomach to reflux into the oropharynx and/or lungs by way of the openings in the outer sheath 160. The second lumen 130 that allows the placement of a smaller feeding tube in the distal stomach and/or post pyloric area. A method of using the Self-Expandable Tube 100 comprises the steps of coupling a catheter body 110 to a self-expandable portion 140 on a distal end of the catheter body 110, the catheter body 110 including a first lumen 120 and second lumen 130 spanning the longitudinal length of the catheter body 110. The first lumen 120 coupling with a tube 122 that traverses the length of the first lumen 120 and through the self-expandable portion 140 and the second lumen 130 coupling with a suction or decompression tube 132 that traverses the length of the second lumen 130 and through the self-expandable portion 140. Creating a sealing membrane by expanding the self-expandable portion 140 to the size of the anatomical lumen. An outer sheath 160 surrounding the longitudinal length of the catheter body 110 including a plurality of openings 170 traversing the outer sheath 160 allowing suctioning from secretions accumulated above the self-expandable portion 140 and the anatomical lumen to travel to the proximal portion of the outer sheath 160. Coupling the proximal portion of the outer sheath 160 to a vacuum or suction source 164 to remove the secretions above the expandable portion 140 and the anatomical lumen by suctioning the secretions through the space 162. The plurality of openings 170 may include a porosity along the outer diameter of the outer sheath 160. Porosity may be varied as to achieve optimum flow through the outer sheath 160 as to not disrupt the portions of the esophagus or stomach or other anatomical lumens in which the outer sheath 160 is disposed. Porosity may also be measured as to the percentage of pores occupying the area of the outer sheath 160. In one embodiment, the porosity may be between 50% and 99%, alternatively, between 60%-89%, alternatively between 70%-79% as to achieve the optimum flow through. The porosity may be increased by further stretching of the outer sheath 160 along the anatomical lumen or esophagus. Additionally, a stretch ratio may be selected for the outer sheath 160 as adjusted to the flow rate in a particular anatomical lumen. For example, the stretching ratio of the outer sheath 160 may be between 1.5 and 10 from the area of the initial outer sheath to the area of the outer sheath 160 stretched in the longitudinal or transverse direction. The outer sheath 160 may include a porosity to achieve a flow rate between 1.0-1000 mL/cm or for a water entry pressure of 0-350 psi selected to a specific vein or artery.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains. Those of skill in the art will understand that obvious variations in construction, materials, dimensions or properties may be made without departing from the scope of the invention which is intended to be limited only by the claims appended hereto.

What is claimed is:

1. A self-expandable tube comprising:
   a. a catheter body operably coupled to a self-expandable portion on a distal end of the catheter body, the catheter body including a first lumen and a second lumen that span a longitudinal length of the catheter body;
   b. an outer sheath surrounding at least a portion of the longitudinal length of the catheter body, and the outer sheath including a plurality of openings traversing a thickness of the outer sheath;
   c. a first lumen is operably coupled with a first tube that traverses the length of the first lumen and through the self-expandable portion;
   d. the second lumen is operably coupled with a second tube that traverses a length of the second lumen and through the self-expandable portion; and
   e. the self-expandable portion expands to a size of the anatomical lumen.

2. The self-expandable tube of claim 1, wherein the plurality of openings are substantially positioned on a distal end of the outer sheath and include a porosity along a outer diameter of the outer sheath which is varied to communicate with a space between the catheter body and the outer sheath to allow fluid flow therebetween and as not to disrupt the anatomical lumen in which the outer sheath is disposed.

3. The self-expandable tube of claim 1, wherein the plurality of openings on the outer sheath allows secretions to be suctioned to a proximal portion of the self-expandable tube.

4. The self-expandable tube of claim 1, wherein a proximal portion of the outer sheath is operably coupled to a vacuum or suction source as to suction a fluid into a space between the catheter body and the outer sheath.

5. The self-expandable tube of claim 1, wherein the second tube is configured to allow suctioning through the self-expandable portion.

6. The self-expandable tube of claim 1, wherein the second tube is configured to allow decompression through the self-expandable portion.

7. The self-expandable tube of claim 1, wherein the second lumen includes a larger diameter than the first lumen.

8. The self-expandable tube of claim 1, wherein the first lumen includes a first one way valve that allows air to flow distally but prevents fluids from flowing proximally, and the second lumen includes a second one way valve that allows air to flow distally but prevents fluids from flowing proximally.

9. The self-expandable tube of claim 1, wherein a plurality of one way valves that allow air to flow distally but prevent fluids from flowing proximally are located along a longitudinal length of the first lumen and the second lumen.

10. The self-expandable tube of claim 1, wherein the first lumen includes a first proximal port located at a proximal end of the first lumen and a first distal port located at a distal end of the first lumen, and the second lumen includes a second proximal port located at a proximal end of the second lumen and a second distal port located at a distal end of the second lumen.

11. The self-expandable tube of claim 1, wherein the self-expandable portion is made of biocompatible material and the outer sheath may abut with the self-expandable portion, the outer sheath conceal the self-expandable portion or the outer sheath may be sealed against the self-expandable portion.

12. The self-expandable tube of claim 1, wherein a proximal portion of the outer sheath is made of a rigid or stiff material and a distal portion is made of a malleable material.

13. The self-expandable tube of claim 1, further comprising a reinforcing member extending longitudinally along the self-expandable portion is coupled to the self-expandable portion.

14. The self-expandable tube of claim 1, further comprising a first positioning mark and a second positioning mark, the first positioning mark provided distally to indicate that the self-expandable portion is in a contracted state, and the second positioning mark provided proximally to indicate that the self-expandable portion is in an expanded state.

15. A method of using the self-expandable tube of claim 1, comprising the steps of:
   a. coupling a catheter body to a self-expandable portion on a distal end of the catheter body, the catheter body including a first lumen and second lumen spanning the longitudinal length of the catheter body;
   b. coupling the first lumen with a tube that traverses the length of the first lumen and through the self-expandable portion and the second lumen coupling with a suction or decompression tube that traverses the length of the second lumen and through the self-expandable portion;
   c. creating a sealing membrane by expanding the self-expandable portion to the size of the anatomical lumen;
   d. surrounding the longitudinal length of the catheter body with an outer sheath with a plurality of openings traversing the outer sheath allowing suctioning from secretions accumulated above the self-expandable portion and the anatomical lumen to travel to the proximal portion of the outer sheath; and
   e. coupling the proximal portion of the outer sheath to a vacuum or suction source to remove the secretions above the expandable portion and the anatomical lumen by suctioning the secretions through the space between the catheter body and outer sheath.

* * * * *